US006931913B2

(12) United States Patent
Manoosingh

(10) Patent No.: US 6,931,913 B2
(45) Date of Patent: Aug. 23, 2005

(54) CHEMICAL AGENT DETECTOR

(75) Inventor: Lane L. Manoosingh, Tampa, FL (US)

(73) Assignee: Constellation Technology Corporation, Largo, FL (US)

( * ) Notice: Subject to any disclaimer, the term of this patent is extended or adjusted under 35 U.S.C. 154(b) by 7 days.

(21) Appl. No.: 10/761,729

(22) Filed: Jan. 21, 2004

(65) Prior Publication Data
US 2005/0155410 A1 Jul. 21, 2005

(51) Int. Cl.[7] ............................................. G01N 29/02
(52) U.S. Cl. .................. 73/31.01; 73/24.01; 73/24.06; 73/31.02; 310/313 R
(58) Field of Search ........................... 73/31.01, 24.01, 73/24.06, 31.02, 31.03; 310/313 R

(56) References Cited

U.S. PATENT DOCUMENTS

| 4,361,026 | A | 11/1982 | Muller et al. | |
|---|---|---|---|---|
| 4,895,017 | A | 1/1990 | Pyke et al. | 73/24.06 |
| 5,325,704 | A | 7/1994 | Mariani et al. | 73/24.06 |
| 5,992,215 | A | 11/1999 | Caron et al. | |
| 6,314,791 | B1 | 11/2001 | Rapp et al. | |
| 6,321,588 | B1 | 11/2001 | Bowers et al. | 73/24.01 |
| 6,442,997 | B1 | 9/2002 | Megerle et al. | |
| 2001/0054305 | A1 | 12/2001 | Banda et al. | |
| 2002/0016004 | A1 | 2/2002 | Nguyen et al. | 436/39 |

Primary Examiner—Daniel S. Larkin
(74) Attorney, Agent, or Firm—Larson & Larson, PA; Herbert W. Larson

(57) ABSTRACT

A chemical agent detector utilizing surface acoustic wave (SAW) sensors for detecting the presence of a multitude of chemical agents by sampling ambient air is provided. A pressure-differential manifold having an air intake port, an exhaust port, a valve and a pump is used to draw the ambient air into the manifold to be tested. A plurality of SAW sensors mounted on sensor driver boards which are in turn mounted on the manifold come into contact with the ambient air sample. Each SAW sensor is coated with a substance that has an affinity for detecting a particular chemical agent. Each SAW sensor driver board generates a continuous RF signal which emits a frequency shift if a particular chemical agent is detected. A power cycler module turns each sensor driver board on and off such that only one sensor driver board is powered-on at a given point in time. An RF multiplexor receives the continuous RF signals generated by the sensor driver boards and outputs one of the RF signals to a microprocessor based upon a timing signal generated by the microprocessor. The microprocessor interprets the frequency shift as the detection of a chemical agent and provides an alarm that a particular chemical agent has been detected.

31 Claims, 5 Drawing Sheets

CHEMICAL AGENT DETECTOR

GOVERNMENT LICENSE RIGHTS

This invention was made with U.S. Government support under contract or grant DTRA02-99-C-0187 awarded by the Defense Treat Reduction Agency. The U.S. Government has certain rights in the invention.

BACKGROUND OF THE INVENTION

1. Field of the Invention

This invention relates to a chemical agent detector. More particularly, it relates to a device used for the detection of chemical agents, vapors and gases which utilizes a plurality of surface acoustic wave (SAW) based sensors in a microcontroller circuit for its sensing and detection functions.

2. Background of the Prior Art

Surface Acoustic Wave (or SAW) based sensors are known in the prior art. SAW sensor devices can be used in the detection of chemical agents, vapors and gases, aerosols and fluids. The detection of chemical agents which may be hazardous to the environment and to the health of living organisms has become very important. The safeguarding of workers in a factory or that of military personnel in hazardous environments has become increasingly important.

The use of SAW sensors for the detection of chemical agents are usually included in local oscillator circuits of detection devices. SAW sensors act as a key resonator in the local oscillator circuit. A polymer coating is deposited on the SAW sensor of which has a specific affinity to a specific gas or fluid to be detected. The oscillator circuit (or loop) is allowed to generate a constant frequency periodic wave. A frequency shift, and/or attenuation, in the oscillator output occurs when there is an introduction of the specific gas or fluid. This frequency shift is measured and used to determine that a specific gas or fluid is present in the environment. The frequency shift is a direct result of a decrease in velocity of the acoustic wave crossing over the SAW resonator. The decrease in velocity of the acoustic wave is a direct result of increased mass loading upon the sensor by molecules of the chemical agent, vapor, gas or fluid. In other words, changes to the propagation characteristics of the acoustic wave can be measured to indicate that the sensor has absorbed (or has been loaded with) a particular chemical agent.

U.S. Pat. No. 4,361,026 to Muller et al. discloses a device and method for sensing fluids wherein a single SAW sensor is employed for detecting a specific targeted fluid. A substrate made of silicon having a piezoelectric film deposited thereon is included on which surface acoustic waves can be propagated. Transmitting and receiving transducers are employed on a top surface of the silicon substrate and piezoelectric film for propagating and receiving the surface acoustic waves. A sensing member is also included along a bottom surface of the silicon substrate to interact with the surface acoustic waves; this causes a variation in the frequency of the wave for measurement by the receiving transducer in response to the presence of the specific targeted fluid. This invention is limited however in its measurement of targeted agents, wherein only one agent, and in particular a fluid, can be measured and detected. A multi-sensor array for the detection of a plurality of different agents is not disclosed or suggested. Further, this prior art invention does not contemplate how to process a high frequency signal that may be generated from the sensing member.

U.S. Pat. No. 4,895,017 to Pyke et al. discloses a device used for the detection of dilute chemical vapors that may be present in the ambient air. This detection device also utilizes SAW based sensors for implementing its detection function. The SAW sensor includes a substrate which is coated with a material selectively absorptive of a group of chemical substances of which the chemical substrate is a member. An electrical signal is produced which is indicative of a change in physical parameters associated with the coated surface in response to the chemical absorption that occurs. An analysis function is connected to the detection circuitry which determines a predicted time constant for diffusion of the detected chemical into the coated substrate and a predicted equilibrium concentration of the detected chemical into the coated substrate as a function of the produced electrical signal. Although this reference does teach the detection of a group of chemicals (that are similar in some way), it does not teach a device which permits the detection of a plurality of chemical agents that are dissimilar and not of the same group which can be detected by cycling a plurality of agent targeted SAW sensors through a multiplexer. Further there is no teaching or disclosure of how a high frequency signal received from the SAW sensor can be rapidly and efficiently processed and measured by a down conversion circuit and mixer. Yet further, there is no mention of utilizing a pressure/differential manifold for its air sampling function.

U.S. Pat. No. 5,325,704 to Mariani et al. discloses a SAW sensor array used for simultaneously detecting several chemical agents. The sensor array employs a bidirectional SAW transducer on a substrate. The substrate also includes several pairs of identical acoustic sensing and referencing channels, each located on opposite sides of the transducer in a mirror image fashion. Each channel is provided with a thin film for absorbing a chemical vapor or gas to be detected and are separated by an acoustic absorber. Also included in each channel is a metallic SAW grating reflector which receives and reflects surface acoustic waves through the film back to the transducer. The reference channels are shielded from ambient conditions while the sensing channels are exposed to the ambient conditions which may have a chemical agent present. An RF signal is applied to the transducer thereby causing an acoustic signal to be propagated through each channel and reflected back through the thin film to the transducer. These output signals are reflected back to the transducer and then detected and measured to see if certain propagation characteristics have changed which would be indicative of the presence of a targeted chemical agent. The specific characteristics include wave velocity and attenuation. This prior art reference improves upon this known type of SAW sensing device by miniaturizing the housing in which it is enclosed. However, this reference does not disclose, let alone teach or suggest, the use of a power cycling scheme with a plurality of SAW sensors to measure and detect a plurality of different chemical agents wherein a multiplexer is used to pass along the readings of the SAW sensors one at a time to a microprocessor for processing and alarm functioning. There is also no disclosure or suggestion of how to measure high frequency signals which may be generated by the SAW sensing device. Still further, there is no disclosure of mounting the SAW sensors on SAW driver boards directly upon a pressure/differential manifold.

Some prior art inventions have addressed power cycling schemes in their use of chemical agent detection devices that employ SAW multi-sensor arrays. This can be seen in U.S. Pat. No. 6,321,588 to Bowers et al. In this reference, a multi-sensor array is provided wherein a power multiplexor is employed to selectively provide power to each of the plurality of sensors at a specific time wherein only one sensor is turned on at any given time. This is done to conserve power and to alleviate cross-talk between the plurality of sensors. Since this reference is concerned with providing a compact detection device, power consumption is of great concern wherein a battery is employed to power the detection device. Since the plurality of sensors are exposed to a common ambient air environment, a need exists with this device to "clean" the sensors after they have been exposed to a chemical agent. The device of this reference addresses this problem by "scrubbing" the air and subsequently exposing the scrubbed air to the sensors. The scrubber utilizes a compound such as charcoal to clean the air sample. Nowhere in this reference does it disclose or teach the use of a novel pressure/differential manifold which can support a plurality of SAW sensors thereby providing a mechanism to expose each sensor to the air to be tested such that each sensor, when powered-on, is exposed to the air to be sampled at that given time and allowed to be analyzed, and then have that air sample evacuated by a pressure build up through the use of a valve in communication with an air intake port of the manifold. Further, this, nor any other prior art device, employs a phase tunable circuit for adjusting the frequencies of the SAW sensors to correct any minor, unwanted, yet inherent, differences that may be present on the polymer coated sensor due to manufacturer characteristics.

Clearly a need exists for an improved chemical agent detector which employs SAW sensing devices. Such a detector should utilize a plurality of SAW sensors that can be controlled by their own oscillator circuits. The sensors should be phase tunable to allow the sensors to be tuned to a more exact frequency than that which is set by the manufacturer. A power cycling scheme in combination with a signal multiplexor should also be incorporated to independently select each sensor such that only one sensor is "on" at any given time and its respective signal is processed at that same given time through a multiplexor. A down conversion element would ensure that all high frequency generated signals can be processed by a microprocessor. Finally, a novel approach to mounting the sensors on a pressure/differential manifold with a valve such that each sensor can be exposed to the air sample would alleviate a need to incorporate complex purging and scrubbing systems to clean the sensors after each air sample exposure.

SUMMARY OF THE INVENTION

I have invented an improved chemical agent detector which utilizes a plurality of SAW sensors. My detector employs a pressure/differential manifold which supports all of the sensors on the frame of the manifold which equates to lower RF noise within the entire detector system and circuit. A pump draws an ambient air sample into the manifold through an air intake port after a valve has opened and allowed the air sample to be exposed to all of the SAW sensors. The air sample is then expelled from the area around the sensors through an exhaust port after traveling along an air channel of the manifold when the valve is closed. The pump remaining on after the valve has closed builds up a pressure which evacuates the air sample out from the manifold as just described. The valve receives a TTL timing signal from a microprocessor of the detector for instructing the valve when to open and close.

Each SAW sensor is configured on a separate printed circuit board and has a complex arrangement of "vias" formed on each board for proper operation and the formation of a very low noise floor, a desired result of this RF sensing system. The SAW driver boards resonate their respective sensor (a coated SAW device) to create a continuous signal at a given frequency (311.5 MHz in the preferred embodiment). Each SAW sensor is phase tunable. The SAW drivers are supplied power by an RF power tuner and cycler which only applies the needed power-on voltage to one of the plurality of sensors at a time. The phase tuner receives a constant voltage from the RF power tuner and cycler. The RF power tuner and cycler also receives its timing signal from the microprocessor which instructs the RF power tuner and cycler to shut down one SAW sensor and provide power to another such that only one sensor is operating at any given time. There is a very short delay between the time one sensor turns off and the next sensor turns on to ensure charge bleed-off and alleviate unwanted harmonics from occurring as the signals of the two sensors pass. Of course unwanted harmonics can add overall noise to the RF system which can effect the sensitivity and response time of the chemical agent detector. Therefore, attenuation is used on each SAW driver board as well as throughout the entire circuit to help reduce RF noise. The timing signal of RF power tuner and cycler, and that of the valve, is a regularly timed, pre-determined, yet can be a user adjustable, signal. However, it would normally be set at the factory depending on the need of the end user.

An RF multiplexor is also provided and is configured to receive all of the output signals of the SAW sensor driver boards. The timing signal that is sent to the RF power tuner and cycler is also sent to the multiplexor thereby ensuring that the RF multiplexor only allows one SAW driver signal to pass through the multiplexor at any given time. Since the timing signals to the RF power tuner and cycler and the RF multiplexor are the same, this ensures that only the active SAW sensor signal is passed onto the microprocessor for analysis and detection functioning. In other words, the microprocessor always knows which sensor signal it is receiving at any given time based upon the simultaneously timing signal generated by the microprocessor and sent to both the RF power tuner and cycler and to the RF multiplexer. The timing signal of the RF power tuner and cycler and the RF multiplexor has the same start and stop time as that of the valve timing signal. This permits all of the sensors of the detector to take a reading of the air sample and each provide a signal in which can be analyzed within the time that the valve is opened and closed.

After a SAW sensor signal is allowed to pass through the RF multiplexor, it is first directed through a mixer for down conversion before it is sent onto the microprocessor. The mixer down converts the raw high frequency signal generated by the SAW driver board to a lower frequency which is suitable for the microprocessor to accept and process. The mixer also provides A/D conversion and digitization of the down converted signal for the microprocessor.

The down conversion is accomplished with the assistance of a local oscillator coupled to the mixer. The local oscillator, acting as a signal generator, outputs a signal whose frequency is slightly higher than that of the SAW sensors. The mixer receives the SAW signal that has passed through the multiplexor and mixes it with the local oscillator frequency to arrive at a predetermined and known down converted signal using super heterodyne architecture. This new down converted signal still contains the same information as the original SAW sensor signal. If one of the SAW sensors has reacted to a chemical agent which it is coated for, it will change the resonance of that SAW driver board and hence change it's signal (i.e., a frequency shift will occur). Once that frequency shifted signal is processed through the multiplexor and the down convertor (i.e., the mixer), the microprocessor will measure this frequency shift and alert the user that the targeted agent has been detected and is present within the air sample. A periphery device, such as a personal computer or laptop, can be used for the alert and alarm functions.

It is therefore a first object of the present invention to provide a SAW based sensor system for detecting a variety of chemical agents, vapors and gases.

It is a further object of the present invention to provide a SAW based sensor system for detecting a variety of chemical agents, vapors and gases which has a fast response time, a high sensitivity, a lower power usage, a compact size and reduced weight all the while inducing as little nosie as possible into the circuit of the system.

It is yet a further object of the present invention to provide a SAW based sensor system for detecting a variety of chemical agents, vapors and gases which has ample bandwidth and tuning capabilities to allow for a wide variety of SAW coatings to be utilized such that a multitude of different chemical agents can be detected.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
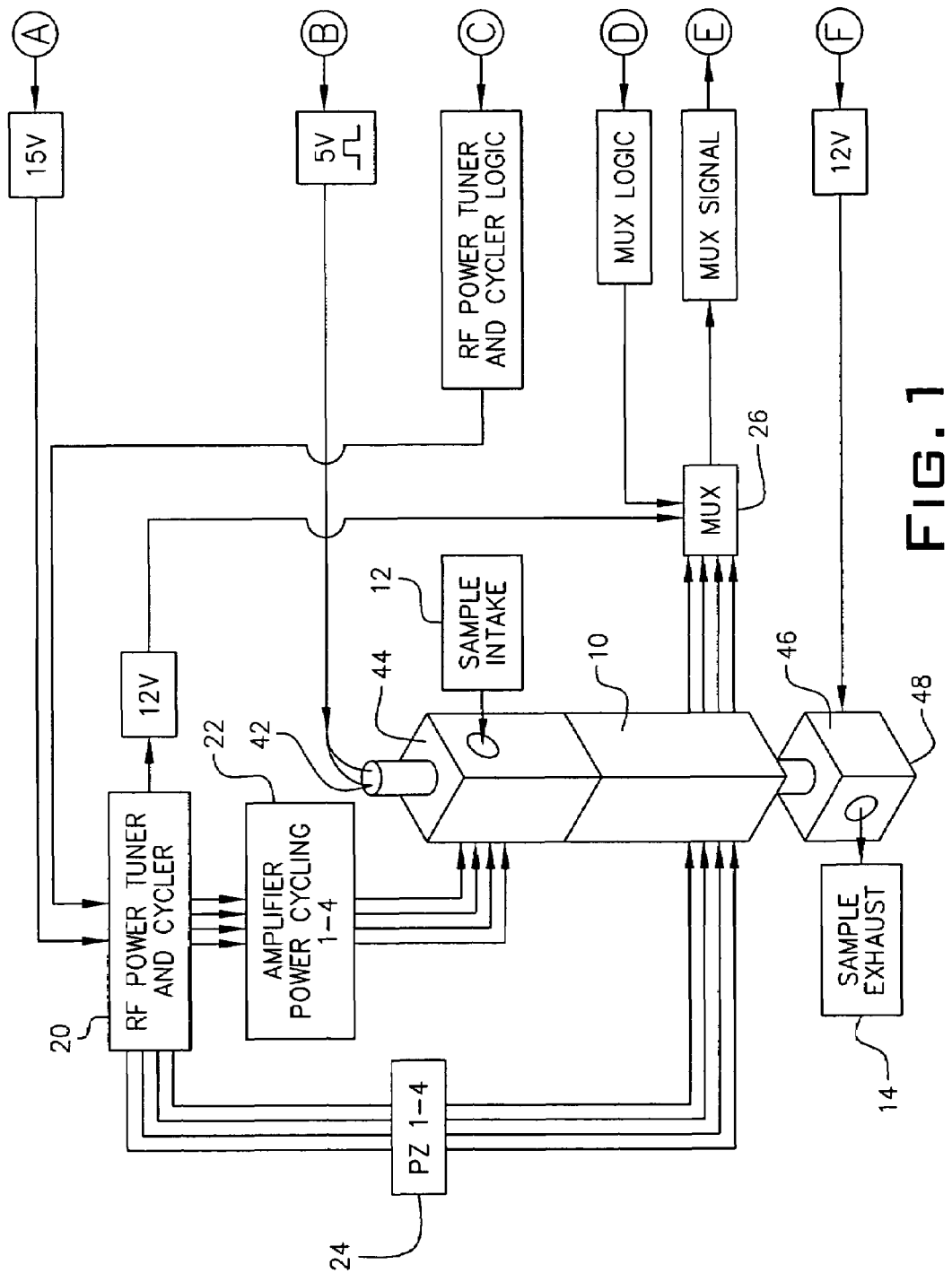
FIG. 1 is a first of two parts of a block diagram illustrating the major components of a chemical agent detector of the present invention.

Throughout the following detailed description, the same reference numerals refer to the same elements in all figures.

Figure 2:
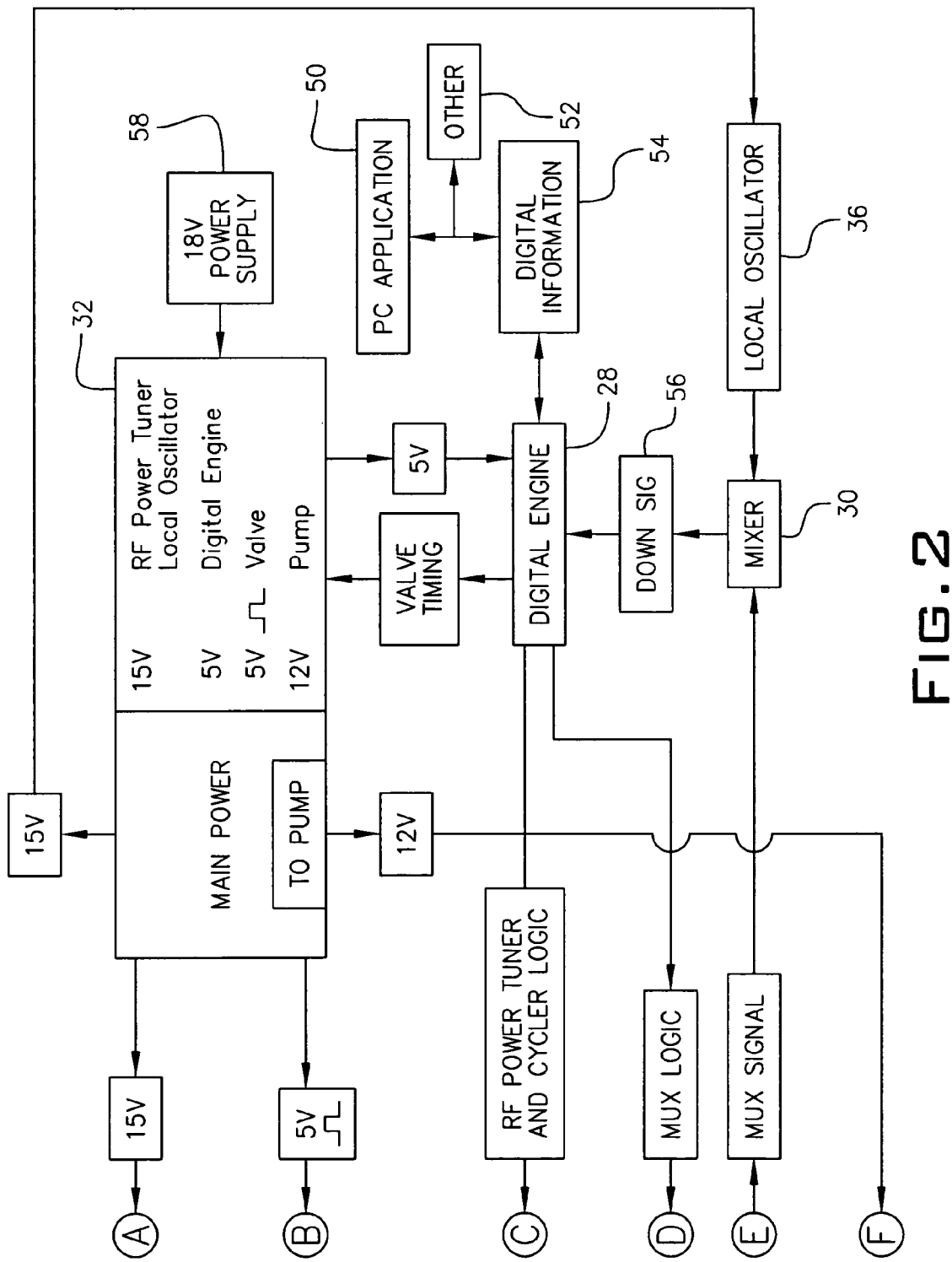
FIG. 2 is the second of two parts of a block diagram illustrating the major components of the chemical agent detector of the present invention.

Referring to FIGS. 1 and 2, a block diagram is shown illustrating the major components of a chemical agent detector of the present invention. In its preferred embodiment, the chemical agent detector of the present invention is enclosed within a small table-top box. However, nothing herein limits that the detector be miniaturized into a small hand-held unit, a pocket sized unit, or even a wristwatch sized unit. And for that matter, nothing herein limits the detector from being a large stand alone mounted within in a building or incorporated within a ventilation system or HVAC system of any sized facility.

FIG. 1 illustrates a first part of the block diagram and FIG. 2 illustrates a second part of the block diagram. The block diagrams of FIGS. 1 and 2 are broken apart onto two sheets since the entire block diagram would not fit onto a single sheet. It is understood however that the encircled letter designations A–F represent a continuous connection between those components located on FIG. 1 and those located of FIG. 2 respectively. The connections between the components of letter designations A–F include voltage signals, logic signals and generated frequency signals used within the circuit of the chemical agent detector of this invention.

With continuing reference to FIGS. 1 and 2, a pressure/differential manifold 10 is shown having an air sample intake port 12 and an air sample exhaust port 14 connected by a continuous air flow pathway 11 (see FIG. 5) along a longitudinal axis of manifold 10. Ambient air that is being sampled for the presence of a chemical agent is drawn into intake port 12 and is expelled through exhaust port 14 after it is sampled by a plurality of sensors mounted on manifold 10 (sensors not shown in FIG. 1). A pump 46 mounted along a bottom portion 48 of manifold 10 draws the air into manifold 10 through intake port 12 and assists in expelling it out through exhaust port 14. Pump 46 is supplied 12 VDC power from a main power board 32 and continuously runs. However, a switch (not shown) can be incorporated in the detector of the present invention which permits the pump to be turned off and on by a user.

Figure 3:
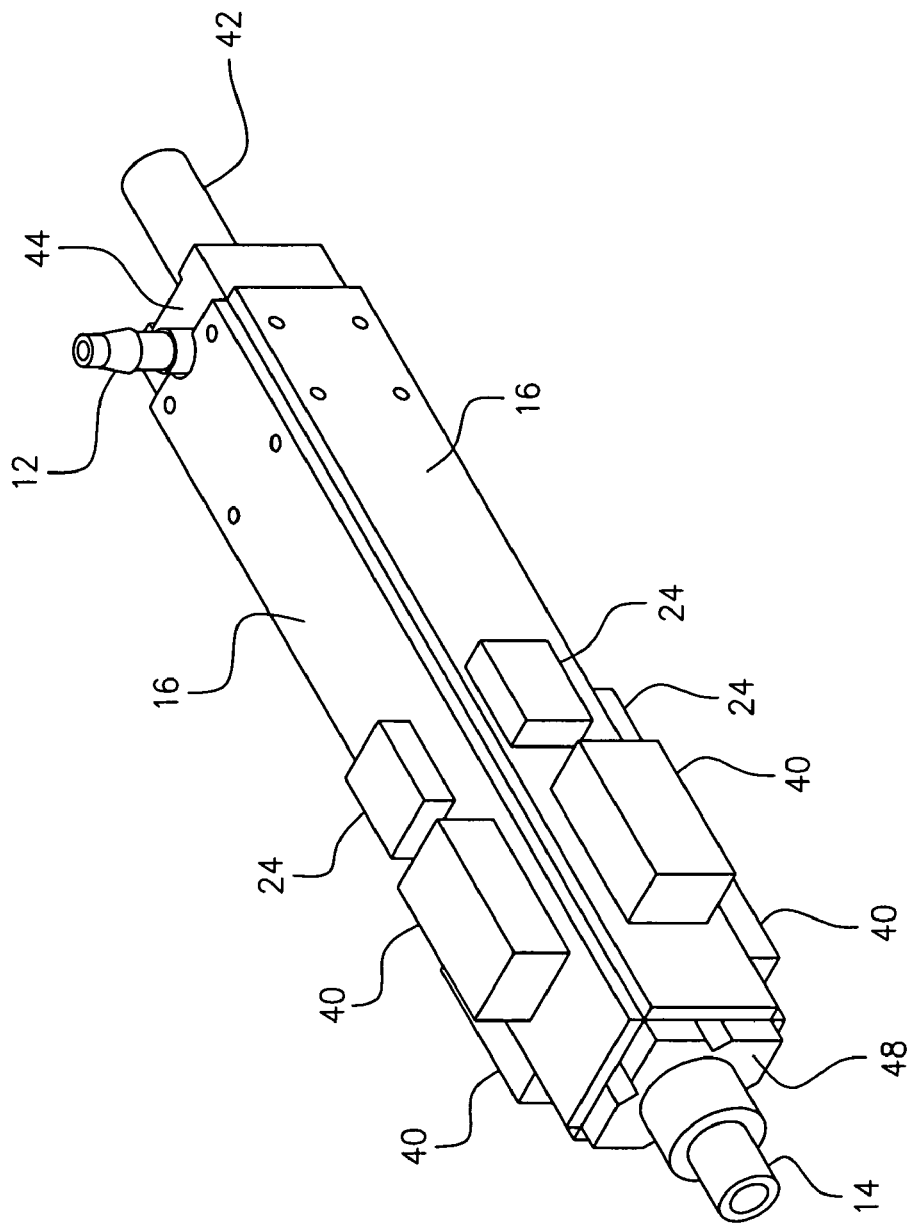
FIG. 3 is a perspective view of a pressure/differential manifold and SAW sensor array employed with the chemical agent detector of the present invention.
Figure 4:
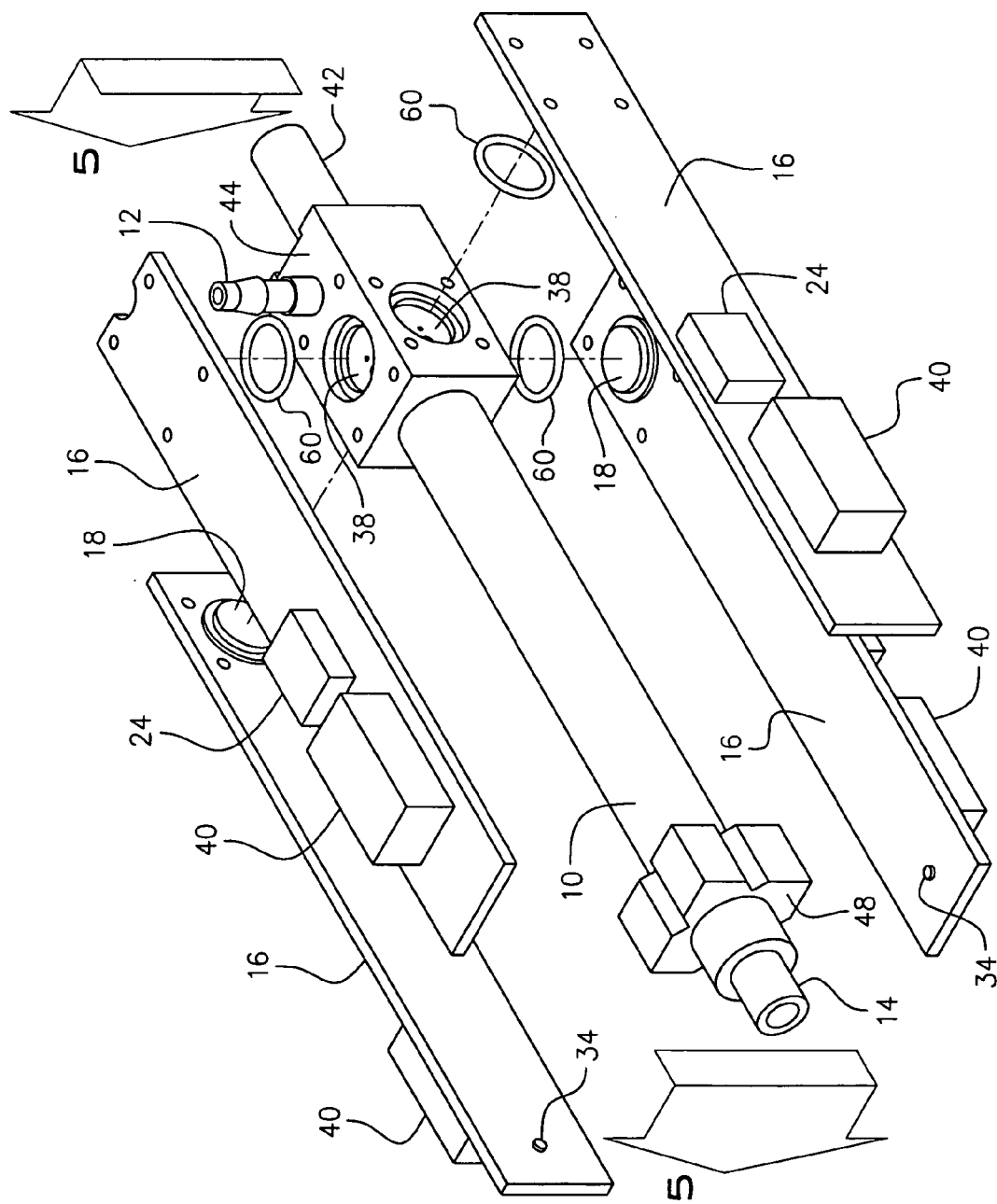
FIG. 4 is an exploded perspective view of the pressure/differential manifold and SAW sensor array employed with the chemical agent detector of the present invention.

With reference to FIGS. 3 and 4, it is shown that manifold 10 has a plurality of SAW driver boards 16 mounted thereupon. The detector of the present invention utilizes RF signals generated by the SAW driver boards 16 to detect the presence of chemical agents in the ambient air. In the preferred embodiment, as shown in FIG. 4, four SAW driver boards 16 are employed. Each SAW driver board 16 employs its own oscillator circuit and is therefor electronically separated from each other board. In other words, the sensors of the detector of the present invention do not use common electronics in their sensing function as widely practiced in the prior art. The four SAW driver boards 16 are mounted on four sides of manifold 10 in a box-like configuration. However, nothing herein limits the use of less than or more than four SAW driver boards 16. Further, nothing herein limits mounting the SAW driver boards 16 in a configuration different than that of a box-like configuration. The mounting of SAW driver boards 16 on manifold 10 helps to reduce noise within the RF system of the detector, a highly desirable result of this RF system. Each SAW driver board 16 has its own SAW sensor 18 mounted upon the board (two of which can be seen in FIG. 4). Each SAW sensor 18 is coated with a particular polymer for detecting four distinct different chemical agents or other toxic vapors. For instance, the four SAW sensors 18 can be separately coated to detect nerve gas, mustard gas, a blistering agent and high vaporous fuels such as diesel and jet fuel. Each SAW sensor 18 inserts within its own cavity 38 formed in a top portion of 44 of manifold 10, as shown in FIG. 4. A set of washers 60 (one for each sensor 18 and cavity 38) are used to assist in seating senors 18 into cavities 38.

Figure 5:
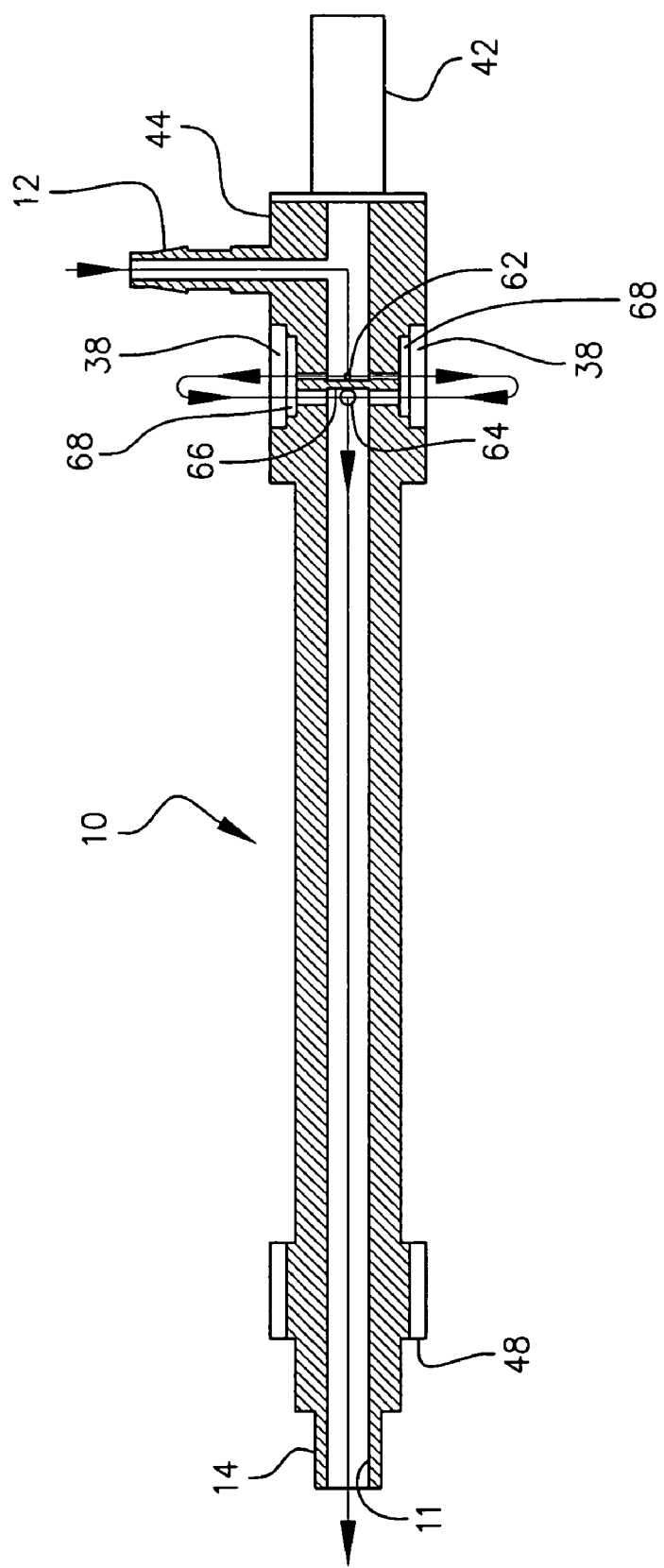
FIG. 5 is a cross-sectional view of the pressure/differential manifold taken along lines 5—5 of FIG. 4.

As shown in FIG. 5, all of the cavities 38 are connected by a common air flow path such that any air sample drawn within manifold 10 through intake port 12 will be exposed to all SAW sensors 18 of the detector of the present invention. FIG. 5 illustrates, by way of a cross-sectional view, how an air sample is drawn into intake port 12 of manifold 10 and exposed to all of the cavities 38 and therefore all of the sensors 18 when each sensor 18 is inserted within each cavity 38. An entrance and exit port, 62 and 64 respectively, are provided for each cavity 38 to permit a portion of the air sample to cross over each sensor 18 inserted with each cavity 38 and then be expelled out through exhaust port 14 down through continues air flow pathway 11. Accordingly, if four sensors 18 are employed along with four cavities 38 formed in manifold 10, then four sets of entrance and exit ports, 62 and 64, are employed within the top portion 44 of manifold 10. As illustrated in FIG. 5, each entrance port 62 has a common proximal end within top portion 44 of manifold 10 in which to permit a portion of the air sample drawn within manifold 10 through intake port 12 by pump 46 to pass into each cavity 38 and over each sensor 18. However, each entrance port 62 also has its own distal end, but which are not common to each other distal end of each other entrance port 62, but instead terminate within the respective cavity 38 to which the entrance port 62 is associated. As further illustrated in FIG. 5, each exit port 64 also has a common proximal end within top portion 44 of manifold 10 in which to permit the portions of the air sample that have crossed over each sensor 18 inserted within each cavity 38 to be expelled out of manifold 10 by way of continuous air flow pathway 11 and exhaust port 14. Accordingly, each exit port 64 also has its own distal end, of which are not common to each other distal end of each other exit port 64. Each distal end of each exit port 64 begins in cavity 38 to which it is associated. A small barrier wall 66 separates all of the proximal ends of the entrance ports 62 from all of the proximal ends of the exits ports 64 such that the sampled air drawn into manifold 10 can be temporarily separated and tested by each sensor 18 and then expelled through the use of pressure (to be discussed hereinafter). A recessed area 68 formed below each cavity 38 is used as an area by each separated portion of the air sample to expose itself to sensor 18 mounted there within. Accordingly, the distal ends of each entrance and exit port 62 and 64 associated with a particular cavity 38 are common to one another in the recessed area 68 associated with a particular cavity 38. A valve 42 mounted upon top portion 44 of manifold 10 works in coincidence with intake port 12, cavities 38, entrance and exit ports 62 and 64, continuous air flow pathway 11 and exhaust port 14 to draw an air sample into manifold 10, expose it to sensors 18 and expel it out of manifold 10 back into the surrounding environment. Full operation of valve 42 will be discussed in further detail hereinafter.

Each SAW driver board 16 resonates its respective SAW sensor 18 to create a continuos high frequency signal when powered-on. In the preferred embodiment, a frequency of about 311.5 MHz is used for each SAW sensor 18. A complex set of "vias" are arranged (formed through) on each SAW driver board 16 to ensure a very low noise floor. Although the "vias" are not necessarily shown in FIGS. 3 and 4, it is understood that each SAW driver board 16 has a multitude of "vias" formed on each board 16 to help reduce RF noise that may be inherent within the system due to the generation of the high frequency RF signals by SAW sensors 18.

With reference now back to FIG. 1, valve 42 is employed along top portion 44 of manifold 10. Valve 42 opens and closes (latches on and off) in response to a 5V TTL timing signal originally generated by a digital engine 28 (see FIG. 2) of the system. Digital engine 28 is a microprocessor and these terms are interchangeable within this description to represent the same component. As shown in FIG. 2, digital engine 28 is programmed to generate a valve timing signal. However, this TTL signal is different (lacks the necessary current) than that which is needed to power the switching on and off functions of valve 42. Accordingly, the valve timing signal is passed through main power board 32 wherein current drivers (not shown) of main power board 32 are employed to complete the switching on and off functions of valve 42 as instructed by digital engine 28. The 5V TTL timing signal shown emanating from main power board 32 along line B from FIG. 2 to FIG. 1 to valve 42 hence has the proper current needed to operate valve 42 along with the instructions as to when to open and close valve 42 and for how long that opening should occur. In the preferred embodiment valve 42 is open for 1.2 seconds.

Pump 46 is powered by 12 VDC from main power board 32. Pump 46 remains "on" at all times and is responsible for drawing an air sample into manifold 10 through intake port 12 when valve 42 is open. Pump 46 is also responsible for expelling the drawn-in air sample out of manifold 10 through exhaust port 14 after it has been tested by sensors 18 by building up a pressure within manifold 10 when valve 42 closes and prohibits any more ambient air from entering manifold 10 through intake port 12.

With continuing reference to FIG. 1, SAW driver boards 16 mounted upon manifold 10 (although not illustrated thereon) are supplied 12 VDC by an RF power tuner and cycler 20 through an amplifier 22. RF power tuner and cycler 20 only applies a "power-on" voltage to one of the four SAW driver boards 16 at a time (a so called power-cycling). This ensures that SAW sensors 18 will not interfere with one another and thereby cause cross-talk. A timing signal, separate from that of the 5V TTL valve timing signal, is applied to RF power tuner and cycler from the digital engine 28 to let it know when to shut down power to one sensor and move onto the next. This timing signal is represented in FIGS. 1 and 2 along line C as RF POWER TUNER AND CYCLER LOGIC. The order of cycling of the sensors does not have to be linear (i.e., from 1 to 4) and can be changed based upon end user requirements by resetting a set of jumpers (not shown) employed within the system of the detector of the present invention. A short delay of about 60 mS is used in between the turning "off" of one sensor and turning "on" of the next sensor in the cycling line to reduce cross-talk that may occur as the signals pass by one another. The start and end times of this timing signal (RF POWER TUNER AND CYCLER LOGIC) are referenced to the same start and end times as that of the 5V TTL valve timing signal. However, these two timing signals are not related in any other manner and are considered separate timing signals. In the preferred embodiment, the RF POWER TUNER AND CYCLER LOGIC signal sends four (4) on/off signals to the four respective oscillator circuits of the four separate SAW driver boards 16 during the 1.2 second period that valve 42 is open. These timing signals can be changed based upon the needs of the end user whereby more than four on/off timing signals may be used for the SAW driver boards 16 if more than four sensors 18 are employed. Further, the length of time that valve 42 remains open may be increased or decreased, again based upon the specific needs of the end user. RF power tuner and cycler 20 receives 15 VDC from main power board 32 as shown along line A in FIGS. 1 and 2.

With continuing reference to FIG. 1, the chemical agent detector of the present invention also includes a phase shifter 24 for each sensor (each SAW sensor board 16 has its own phase shifter 24). Phase shifters 24 receive a constant 12 VDC power source from RF power tuner and cycler 20. It is desirable to provide a constant voltage source to phase shifter 24 because of the measurable delay that occurs when turning on the varactor diodes present on each SAW driver board 16. Phase shifters 24 are used to compensate for any non-uniformity of the SAW coating deposited on each SAW sensor 18 by tuning each sensor to an exact frequency. For instance, in the preferred embodiment, 311.5 MHz is employed (although other frequencies could be employed). However, not every SAW sensor can necessarily be manufactured to generate this exact frequency and therefore phase shifters 24 are employed. FIG. 1 illustrates phase shifters 24 as being detached from manifold 10. This was done to clarify the function of each phase shifter 24. In actuality, one each phase shifter 24 is located on one each SAW driver board 16 as shown in FIGS. 3 and 4.

As shown in FIG. 4, each driver board 16 also contains isolation attenuation in the form of an attenuator 34 for obstructing any signal from leaking back (similar to the action of a diode) through a mixer from a local oscillator (both to be discussed in further detail hereinafter). Attenuator 34 also reduces tiny spikes that occur during power-up of each SAW driver board 16. In the preferred embodiment, a 3 db attenuator is employed on each SAW driver board 16. If such attenuation were not used, it could result in the de-tuning of SAW driver board 16, which would effectively shut it down. This potential for de-tuning occurs because the local oscillator frequency is so close in value to the SAW sensor generated frequency. In fact, in the preferred embodiment, the difference between the two frequencies can be as little as 400–5500 kHz.

Additional attenuation is used through out the circuitry of the chemical agent detector of the present invention. In this RF system, lowering the noise floor is highly desirable. In the chemical agent detector of the present invention, lowering the noise floor throughout the system is balanced with sensitivity and response time for the device. In the preferred embodiment, this chemical agent detector has a very high sensitivity to any agent that it is programmed to detect along with a very fast response time. To achieve such, noise inherent in the RF system must be balanced against these two functions. Accordingly, the amount nosie, the sensitivity of the detector and the response time to which it reacts must be balanced against the amount of attenuation that must be placed between the signal line and that of the input of the controller (the digital engine 28) to achieve a so-called "sweat-spot". Increasing attenuation can lower the amplitude of an incoming wave of a signal being directed to the digital engine. This can lead to decreasing the "Valuable Signal Amplitude", which can lead to less counting by the controller (digital engine 28) which in turn results in waiting longer to react to the sensing of an agent present in the ambient air (a reduction in response time). Also, by reducing the "Valuable Signal Amplitude", small frequency shifts may be missed which may lead to missing small amounts of chemical agents being present in the ambient air (a decrease in sensitivity). On the other hand, allowing a lot of noise to be added to the signal being processed, results in an overall degradation of the frequency of the signal that is being analyzed by digital engine 28. This can also lead to a decrease in sensitivity and a reduction in response time. Accordingly, the preferred embodiment of the present invention utilizes a proper amount of attenuation to achieve a high level of sensitivity and a very fast response time with an acceptable noise floor.

Referring to FIGS. 3 and 4, each SAW driver board 16 also contains a low pass filter 40 for permitting frequencies generated by sensor 18 that are only below 380 MHz from passing through SAW driver board 16. This ensures that any second harmonic frequencies (approximately 624 MHz in the preferred embodiment) from being added to the signal that is passed on to digital engine 28.

With reference back to FIG. 1, once a signal is generated by one of the four sensors, it is passed along to the RF multiplexor (MUX) 26. MUX 26 receives 12 VDC also from RF power tuner and cycler 20. The RF MUX 26 allows only one of the SAW driver signals to pass through to the digital engine 28 (the microprocessor)—reference now also to FIG. 2—because microprocessor 28 has only a single input signal port and therefore can only be feed one signal at a time. MUX 26 and RF power tuner and cycler 20 receive the same timing signal from digital engine 28. MUX 26 is timed to allow the signal from the single SAW sensor driver board 16 which is presently active, through to the processor (digital engine 28). The MUX timing signal is represented in FIGS. 1 and 2 as MUX LOGIC along line D between digital engine 28 and MUX 26. The MUX LOGIC timing signal also has the same start and end time as that of the 5V TTL valve timing signal but is not related to the valve timing signal in any other manner. Conversely, the MUX LOGIC and the RF POWER TUNER AND CYLCER timing signals are exactly the same and can even be placed on the same pin controller of digital engine 28 if desired. Accordingly, the MUX LOGIC timing signal is receiving four on/off commands as to which sensor signal it is to receive and output to digital engine 28 within the 1.2 seconds that valve 42 is open.

With continuing reference to FIGS. 1 and 2, after a single SAW driver board 16 signal is allowed to pass through MUX 26 (depending on which sensor is turned on at that given point), it is first passed through to a mixer 30 (a down conversion module) before being allowed to enter digital engine 28. The mixer 30 decreases (down converts) the raw frequency of the SAW driver board 16 that has passed through mixer 30 at that given point in time to a lower frequency signal which is more suitable for microprocessor 28 to accept. Only a single downconversion is employed in the preferred embodiment so as to avoid the introduction of broad band noise to the circuit. More than one down conversion could be employed if needed.

Mixer 30 accomplishes this downconversion through the assistance of a local oscillator 36. Local oscillator 36, acting as a signal generator, outputs a signal whose frequency is slightly higher than that of the SAW driver board 16. In the preferred embodiment, local oscillator outputs a 312 MHz signal. Mixer 30 takes the SAW driver board signal it has received at a frequency of 311.5 MHz and subtracts the local oscillator signal of 312 MHz to arrive at a new signal of 500 kHz (super heterodyne architecture). Local oscillator 36 receives 15 VDC directly from main power supply 32.

This new downconverted 500 kHz signal still contains the same information that the original 311.5 MHz signal that a given SAW driver board 16 contained (i.e., information relating to the detection of any chemical agents that may be present in the air of the environment being sampled). The down converted frequency signal (shown as DOWN SIG in FIG. 2) is feed to microprocessor 28 (the digital engine) and processed to determine whether sensor 18 of SAW driver board 16 is resonating. If a sensor 18 detects a chemical agent, it will change its resonance thereby changing its output frequency (a shift in frequency) of SAW driver board 16. This results in a change to the output of mixer 30, which will be processed by microprocessor 28. For example, if SAW driver board 16 changes its frequency from 311.5 MHz to 311.4 MHz, due to the detection of a targeted chemical agent being loaded upon SAW sensor 18, the output of mixer 30 would fluctuate from 500 KHz to 600 KHZ. This signal is being constantly supplied to microprocessor 28 which is constantly sampling all down converted inputted signals it receives from MUX 26 through mixer 30. Processor 28 can be connected to one of many of different types of peripheral devices such as a PC, laptop or PDA (personal digital assistance) or other like computing devices. These devices are represented in FIG. 2 as PC APPLICATION 50 and OTHER 52. The computing device or devices can have one or more alert functions which indicate that there has a been a frequency shift (in the above set forth example a 100 kHz frequency shift). Thus the detection of at least one of the targeted chemical agents has been discovered. However, more than one agent could be detected. In fact, four agents could be detected at one time in the preferred embodiment. The box representing DIGITAL INFORMATION 54 in FIG. 2 contains the alert signal or function. As also shown in FIG. 2, PC APPLICATION 50 is a bi-directional connection which permits PC APPLICATION 50 to communicate with digital engine 28 through DIGITAL INFORMATION 54 and update the digital engine 28 firmware, if necessary, or to perform diagnostic functions thereupon.

With continuing reference to FIG. 2, the chemical agent detector of the present invention contains main power board 32, as previously discussed, which supplies a multitude of different voltages to all other boards and components of the detector. Main power board 32 is supplied power by an 18 VDC power supply 58.

Equivalent elements can be substituted for the ones set forth above such that they perform in the same manner in the same way for achieving the same result.

What is claimed is:

1. A chemical agent detector for sensing and detecting the presence of a multitude of different chemical agents through the utilization of surface acoustic wave (SAW) sensors by taking an ambient air sample from an environment, the chemical agent detector comprising:
    a) a manifold having an air intake port and an air exhaust port through which the ambient air sample can be drawn within the manifold and tested for the presence of the multitude of different chemical agents and then expelled, the ambient air sample drawn within the manifold by a pump connected to the manifold,
    b) a plurality of sensor driver boards mounted on the manifold,
    c) a plurality of SAW sensors, one each mounted on each sensor driver board such that they are in contact with the ambient air sample drawn within the manifold, each SAW sensor coated with a substance that has an affinity for detecting a particular chemical agent, each SAW sensor and sensor driver board generating its own continuous RF signal which can emit a frequency shift of the continuous RF signal if the particular chemical agent to which the SAW sensor has an affinity for detecting is loaded upon the SAW sensor by the ambient air sample,
    d) an RF power tuner and cycler for selectively applying power to the plurality of SAW sensors such that only one SAW sensor is powered-on at a given point in time, the RF power tuner and cycler electrically coupled to the plurality of SAW sensors mounted on the sensor driver boards,
    e) an RF multiplexor for receiving the continuous RF signals generated by the SAW sensors and sensor driver boards and for outputting only one of the RF signals at a time based upon which SAW sensor is powered-on at the given point in time, the RF multiplexor electrically coupled to the plurality of sensor driver boards, the RF multiplexor receiving a constant voltage from the RF power tuner and cycler,
    f) a microprocessor for interpreting the RF signals generated by the SAW sensors and sensor driver boards and for detecting whether a frequency shift has occurred in any of the generated RF signals which would be indicative of the presence of a particular chemical agent in the ambient air sample drawn within the manifold, the microprocessor electrically coupled to the RF power tuner and cycler and the RF multiplexor, the microprocessor generating a timing signal to the RF power tuner and cycler and the RF multiplexor for instructing the RF power tuner and cycler when and in which order to power-on and power-off each of the plurality of SAW sensors and sensor driver boards such that the RF multiplexor receives and outputs an RF signal which is generated by only one of the plurality of SAW sensors and sensor driver boards that are turned-on at the given point in time as instructed by the microprocessor, and
    g) a power supply including a main power board for providing power to the RF power tuner and cycler, the microprocessor and the pump.

2. The chemical agent detector of claim 1, further comprising the manifold having a continuous air flow pathway along a longitudinal axis of the manifold connecting the air intake port with the air exhaust port at top and bottom ends respectively of the manifold.

3. The chemical agent detector of claim 1, further comprising a valve mounted along a top end of the manifold proximal to the air intake port, the valve electrically coupled to the microprocessor for receiving a valve timing signal from the microprocessor, the valve timing signal having a start time and an end time equal to that of the timing signal generated and directed to the RF power tuner and cycler and the RF multiplexor, the valve electrically coupled to the main power board of the power supply.

4. The chemical agent detector of claim 3, wherein all of the plurality of SAW sensors and sensor driver boards are powered on and off within the period of time that the valve is open and closed.

5. The chemical agent detector of claim 3, wherein current drivers of the main power board of the power supply are employed to open and close the valve in accordance with the valve timing signal generated by the microprocessor.

6. The chemical agent detector of claim 3, wherein the valve periodically closes the air intake port temporarily while the pump continues to run to establish a pressure build-up within the manifold to evacuate the ambient air sample present within the manifold out through the air exhaust port.

7. The chemical agent detector of claim 1, further comprising a plurality of phase shifters, one each for each of the plurality of SAW sensors, each phase shifter tuning one each SAW sensor such that all of the continuous RF signals generated by the SAW sensors and sensor driver boards are of equal value.

8. The chemical agent detector of claim 7, wherein the plurality of phase shifters receive a constant voltage from the RF power tuner and cycler.

9. The chemical agent detector of claim 1, wherein the continuous RF signals generated by the SAW sensors and sensor driver boards is 311.5 MHz.

10. The chemical agent detector of claim 1, further comprising a plurality of amplifiers coupled intermediate the RF power tuner and cycler and the plurality of SAW sensors and sensor driver boards, one amplifier provided for each SAW sensor and each sensor driver board employed within the detector, the amplifiers assisting the SAW sensors and sensor driver boards in generating the continuous RF signal, the amplifiers receiving a voltage from the RF power tuner and cycler which cycles on and off in accordance with the timing signal generated by the microprocessor and applied to the RF power tuner and cycler.

11. The chemical agent detector of claim 1, further comprising a down conversion module electrically coupled between the RF multiplexor and the microprocessor for down converting the RF signal outputted from the RF multiplexor before it is directed to the microprocessor, the down conversion module electrically coupled to the main power board of the power supply.

12. The chemical agent detector of claim 11, wherein the down converted signal is approximately 500 kHz.

13. The chemical agent detector of claim 11, wherein the down conversion module includes a mixer and a local oscillator, the mixer receiving the RF signal generated by the SAW sensor and sensor driver board that is currently power-on and passed through the RF multiplexor and a constant signal generated by the local oscillator, thereafter subtracting the two received signals to arrive at the down converted signal of which is an output signal of the mixer directed to the microprocessor.

14. The chemical agent detector of claim 13, wherein the output signal of the mixer will change due to a frequency shift of the RF signal generated by the SAW sensor and sensor driver board in response to a chemical agent being detected by one of the plurality of SAW sensors to which it has an affinity to detect.

15. The chemical agent detector of claim 1, wherein the microprocessor is connected to an alarm device for indicating that a chemical agent to which the chemical agent detector is programmed to sense and detect has been detected in the ambient air sample of the environment.

16. The chemical agent detector of claim 1, wherein each of the plurality of SAW sensors along with one each of the sensor driver boards represents its own oscillator circuit which is electronically isolated from each other SAW sensor and sensor driver board.

17. The chemical agent detector of claim 1, wherein four sensor driver boards are employed, each sensor driver board having one SAW sensor mounted thereupon.

18. The chemical agent detector of claim 1, wherein the manifold has a top portion in which are formed a plurality of cavities, one each cavity for one each SAW sensor employed with the chemical agent detector.

19. The chemical agent detector of claim 18, wherein each cavity includes a top and bottom area, the top area receiving the SAW sensor inserted there within, the bottom area remaining open for receiving a portion of the ambient air sample when drawn within the manifold.

20. The chemical agent detector of claim 19, further comprising:
a) a plurality of entrance port and exit port sets, one set each for each cavity employed with the chemical agent detector, each entrance port and exit port having proximal and distal ends, all of the proximal ends of each of the entrance ports common to an area within the manifold wherein the ambient air sample has been drawn within the manifold through the air intake port by the pump, and all of the proximal ends of each of the exit ports common to an area within the manifold wherein the ambient air sample has already passed over the SAW sensors, and
b) a barrier wall inserted within the top portion of the manifold separating the entrance port proximal ends from the exit port proximal ends.

21. The chemical agent detector of claim 20, wherein the distal ends of each entrance and exit port of one set of entrance and exit ports are common to one of the bottom areas of one cavity such that a portion of the ambient air sample can cross over a SAW sensor and be tested for a particular chemical agent and thereafter be expelled out of the manifold.

22. The chemical agent detector of claim 1, further comprising:
a) a plurality of attenuators, one each for each sensor driver board employed with the chemical agent detector, each attenuator mounted on each sensor driver board, and
b) a plurality of low pass filters, one each for each sensor driver board employed with the chemical agent detector, each low pass filter mounted on each sensor driver board, the low pass filter ensuring that any harmonics generated above the frequency of the RF signal generated by a SAW sensor and sensor driver board to which the low pass filter is associated with does not interfere with the RF signal.

23. A chemical agent detector having a circuit including surface acoustic wave (SAW) sensors for detecting the presence of varied chemical agents by sampling ambient air of an environment in which the detector is located, the chemical agent detector comprising:
a) a pressure-differential manifold having an air intake port located at a top portion and an air exhaust port located at a bottom portion connected by a continuous air flow pathway formed through the manifold along a longitudinal axis thereof, the manifold further including a pump used to draw the ambient air into the manifold through the air intake port for testing for the presence of the varied chemical agents and then expelling the tested ambient air out of the manifold through the exhaust port,
b) a plurality of SAW sensor driver boards mounted on the manifold, each SAW sensor driver board having its own SAW sensor mounted thereon such that all SAW sensors come into contact with the ambient air drawn into the manifold by the pump, each SAW sensor coated with a substance that has an affinity for detecting a particular chemical agent, each SAW sensor driver board generating its own continuous RF signal which emits a frequency shift of the continuous RF signal if the particular chemical agent to which the SAW sensor has an affinity for detecting is loaded upon the SAW sensor of a particular SAW sensor driver board by the sample of ambient air,
c) an RF power tuner and cycler for selectively applying a voltage signal to the plurality of SAW sensor driver boards such that only one SAW sensor driver board is powered-on at a given point in time and therefore only one RF signal is being generated at that given point in time, the RF power tuner and cycler electrically coupled to the plurality of SAW sensor driver boards,
d) an RF multiplexor for receiving the continuous RF signals generated by the SAW sensor driver boards and for outputting only one of the RF signals at a time based upon which SAW sensor driver board is powered-on at the given point in time, the RF multiplexor electrically coupled to an output of the plurality of SAW sensor driver boards, the RF multiplexor also electrically coupled to the RF power tuner and cycler and receiving a constant voltage signal therefrom,
e) a microprocessor for interpreting the RF signals generated by the SAW sensor driver boards and for detecting whether a frequency shift has occurred in any of the generated RF signals which would be indicative of the presence of a particular chemical agent in the sample of ambient air drawn within the manifold, the microprocessor electrically coupled to the RF power tuner and cycler and the RF multiplexor, the microprocessor generating a timing signal to the RF power tuner and cycler and the RF multiplexor for instructing the RF power tuner and cycler when and in which order to power-on and power-off each of the plurality of SAW sensor driver boards such that the RF multiplexor receives and outputs an RF signal which is generated by only one of the plurality of SAW sensor driver boards that is turned-on at the given point in time as instructed by the microprocessor, f) a valve mounted along the top end of the manifold proximal to the air intake port, the valve electrically coupled to the microprocessor for receiving a valve timing signal from the microprocessor, the valve timing signal having a start time and an end time equal to that of the timing signal generated and directed to the RF power tuner and cycler and the RF multiplexor, the valve working in coincidence with the pump such that when the valve is closed a pressure build-up occurs within the manifold as the pump continues to run thereby expelling the sample of ambient air that has been tested out from the manifold through the exhaust port, and g) a power supply including a main power board for providing power to the RF power tuner and cycler, the microprocessor, the valve and the pump.

24. The chemical agent detector of claim 23, further comprising a plurality of phase shifters, one each for each of the plurality of SAW sensor driver boards, each phase shifter tuning one SAW sensor such that all of the continuous RF signals generated by the SAW sensor driver boards have an equal value, the plurality of phase shifters electrically coupled to the RF power tuner and cycler and receiving a constant voltage therefrom.

25. The chemical agent detector of claim 23, further comprising a plurality of amplifiers coupled intermediate the RF power tuner and cycler and the plurality of SAW sensor driver boards, one amplifier provided for each SAW sensor driver board employed within the detector, the amplifiers assisting the SAW sensor driver boards in generating the continuous RF signal, the amplifiers receiving a cycling voltage from the RF power tuner and cycler in accordance with the timing signal generated by the microprocessor and applied to the RF power tuner and cycler.

26. The chemical agent detector of claim 23, further comprising a down conversion module electrically coupled between the RF multiplexor and the microprocessor for down converting the RF signal outputted from the RF multiplexor before it is directed to the microprocessor, the down conversion module including a mixer and a local oscillator, the mixer receiving the RF signal generated by the SAW sensor driver board that is currently powered-on and passing through the RF multiplexor and a constant RF signal generated by the local oscillator, thereafter subtracting the two received RF signals to arrive at the down converted RF signal of which is an output signal of the mixer and is directed to the microprocessor, the down conversion module electrically coupled to the main power board of the power supply.

27. The chemical agent detector of claim 26, wherein the output signal of the mixer will change due to a frequency shift of the RF signal generated by the SAW sensor driver board in response to a chemical agent being detected by one of the plurality of SAW sensors to which it has an affinity to detect.

28. The chemical agent detector of claim 23, wherein the manifold has a plurality of cavities formed in the top portion, one cavity for each SAW sensor employed with the chemical agent detector, each cavity including a top and bottom area, the top area receiving the SAW sensor of a SAW sensor driver board inserted there within, the bottom area remaining open for receiving a portion of the sample of ambient air drawn within the manifold by the pump.

29. The chemical agent detector of claim 23, further comprising:

a) one entrance port and exit port set for each cavity formed in the manifold top portion, each entrance port and exit port set having proximal and distal ends, all of the proximal ends of all of the entrance ports common to an area within the manifold wherein the sample of ambient air has been drawn within the manifold through the air intake port by the pump, and all of the proximal ends of all of the exit ports common to an area within the manifold wherein the sample of ambient air has passed over the SAW sensors of the SAW sensor driver boards, and b) a barrier wall inserted within the top portion of the manifold separating all of the entrance port proximal ends from all of the exit port proximal ends.

30. The chemical agent detector of claim 29, wherein the distal ends of each entrance and exit port set are common to one of the bottom areas of one cavity such that a portion of the sample of ambient air crosses over a SAW sensor of a SAW sensor driver board and is tested for a particular chemical agent and thereafter expelled down through the continuous air flow pathway and out of the exhaust port of the manifold.

31. The chemical agent detector of claim 23, further comprising:

a) a plurality of attenuators, one for each SAW sensor driver board and mounted thereupon, and b) a plurality of low pass filters, one for each SAW sensor driver board and mounted thereupon, the low pass filter of each SAW sensor driver board ensuring that any harmonics generated above the frequency of the RF signal generated by the SAW sensor driver board does not interfere with the RF signal generated by the SAW sensor driver board.

* * * * *